(12) United States Patent
Kamataki et al.

(10) Patent No.: US 8,983,613 B2
(45) Date of Patent: Mar. 17, 2015

(54) METHOD AND MONITOR APPARATUS FOR DISPLAYING PARAMETERS INDICATIVE OF MUSCLE RELAXATION

(75) Inventors: Osamu Kamataki, Tokyo (JP); Masami Tanishima, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1308 days.

(21) Appl. No.: 11/442,335

(22) Filed: May 30, 2006

(65) Prior Publication Data

US 2006/0270943 A1 Nov. 30, 2006

(30) Foreign Application Priority Data

May 27, 2005 (JP) ................ P2005-155664

(51) Int. Cl.
*A61N 1/36* (2006.01)
*A61B 5/0488* (2006.01)
*A61B 5/11* (2006.01)
*A61B 5/00* (2006.01)

(52) U.S. Cl.
CPC .......... *A61B 5/0488* (2013.01); *A61N 1/36003* (2013.01); *A61B 5/1107* (2013.01); *A61B 5/6824* (2013.01); *A61B 2562/0219* (2013.01); *A61B 5/6825* (2013.01)
USPC ....................................... 607/48

(58) Field of Classification Search
CPC ................................ A61N 1/36003
USPC ....................................... 607/48
See application file for complete search history.

(56) References Cited

U.S. PATENT DOCUMENTS

| 6,389,312 B1 * | 5/2002 | Duckert ................. 600/546 |
| 6,725,086 B2 * | 4/2004 | Marinello .............. 600/544 |
| 2004/0254617 A1 * | 12/2004 | Hemmerling et al. .......... 607/48 |

FOREIGN PATENT DOCUMENTS

| JP | 58-133233 A | 8/1983 |
| JP | 1-259841 A | 10/1989 |
| JP | 10-57320 A | 3/1998 |

OTHER PUBLICATIONS

"TOF Watch SX" http://web.archive.org/web/20031219055136/http://bluestarent.com/tofwatch/tofwatchsx.html. Dated Dec. 19, 2003.*
"Neuromuscular Junction Monitoring for the Organon Protocol 19.4. 308 Suggamedex Trial".*
Mitsui et al. "Correlation between High Temperature Dependence of Smooth Muscle Myosin Light Chain Phosphatase Activity and Muscle Relaxation Rate" Journal of Biological Chemistry, vol. 268, No. 8, pp. 5842-5848, Feb. 25, 1994.*
"TOF Watch", pp. 2-6, published Jan. 2000.
Japanese Office Action, dated Oct. 5, 2010, issued in counterpart Application No. 2005-155664.

* cited by examiner

*Primary Examiner* — Eric D. Bertram
(74) *Attorney, Agent, or Firm* — Sughrue Mion, PLLC

(57) ABSTRACT

A stimulator is adapted to electrically stimulate a muscle of a patient. A detector is adapted to detect a response of the stimulated muscle. A processor is operable to obtain a plurality of parameters indicative of muscle relaxation of the patient based on the detected response. A display is operable to display the parameters simultaneously while showing chronological changes thereof.

6 Claims, 5 Drawing Sheets

METHOD AND MONITOR APPARATUS FOR DISPLAYING PARAMETERS INDICATIVE OF MUSCLE RELAXATION

CROSS-REFERENCE TO RELATED APPLICATIONS

This application claims priority from Japan Patent Application No. 2005-155664.

BACKGROUND OF THE INVENTION

The present invention relates to a method and a monitor apparatus for displaying parameters indicative of muscle relaxation.

Examples of measurement and monitoring items required for medical care of a patient undergoing surgical procedures include blood gases, movements of the circulatory system, respiration, anesthetic depth, and muscle relaxation. Among these items, parameters which can be monitored in a real time manner include electrocardiogram output, blood pressure, $SpO_2$, body temperature, heart rate, respiratory rate, and the like.

Accordingly, monitoring a muscle relaxation state of a patient undergoing surgical procedures is also an extremely important issue. From the above viewpoint, a nerve stimulation system has conventionally been employed as an apparatus for monitoring a muscle relaxation state. The nerve stimulation system is configured so as to stimulate an ulnar nerve of a patient, and measure contraction of an adductor muscle of the thumb in response to the stimulation. As examples of an apparatus of this type for monitoring a muscle relaxation state, there has generally known an apparatus of a type which measures changes in a measured myogenic potential, and an apparatus of another type which measures kinetic effects deriving from muscle contraction (e.g., measuring an acceleration of muscular response).

The following methods have been adopted as stimulation patterns for detecting and measuring a muscle relaxation state by electric stimulator.

(1) Single Stimulation Method: a stimulation method of applying stimulating current of 200 microsecond at intervals of one or ten seconds, thereby applying single stimulation.

(2) TOF (train of four) Method: a stimulation method of applying stimulation trains at 15-second intervals, each train constituted of four repeated stimuli at 0.5 second intervals. In the TOF method, a ratio (a TOF ratio) between the height of the first stimulation and that of the fourth stimulation is expressed in %, which reaches 100% when the administered muscle relaxant is not exerting any effect.

(3) DBS (double burst signal) Method: a stimulation method of generating a stimulation train, generally constituted of three stimuli at 20 millisecond intervals, and another train after 0.75 second, thereby determining a difference in responses to these two burst signals by hand (palpation).

(4) PTC (post tetanic count) Method: a stimulation method to be employed when a response to the stimulation applied by the single stimulation method and the TOF method is completely faded under a state of deep muscle relaxation. First, stimulation at 1 Hz is applied for 15 cycles. When no response to the stimulation is ascertained, tetanic stimulation is applied. Subsequently, after three seconds, by stimulation at 1 Hz is applied for 15 cycles. Timing when a response to the TOF stimulation emerges next is estimated on the basis of the number of evoked responses.

(5) Tetanic Stimulation Method: a stimulation method of making an evaluation by palpation on the basis of tetanic stimulation, in accordance with which stimulation at 50 or 100 Hz is applied for only five seconds.

The related-art apparatus for monitoring and displaying muscle relaxation state has a function of simply displaying the timing of electric stimulation and a degree of a change in the acceleration of a muscle with respect to time. However, the apparatus involves a problem, in that it lacks a function of monitoring timing at which a muscular relaxant is administered, thereby being unable to ascertain a chronological relationship between administration of a drug and changes in an acceleration of a muscle. Therefore, the related-art apparatus of this type has failed to accurately ascertain a duration between administration of a drug and timing at which the drug starts to exert its effect, or the like.

In view of the above, Japanese Patent Publication No. 10-57320A discloses a monitor apparatus in which event data such as an event pertaining to administration of a muscle relaxant can be input, and there are displayed the timing that the event is occurred and a timing and a magnitude of a response of an electrically stimulated muscle.

However, in the above monitor apparatus, among parameters indicative of the muscle relaxation, such as a TOF ratio, a TOF count, and a PTC, are to be displayed on a monitor screen, only a single parameter is displayed in the form of a numerical value or a graph. Accordingly, it is impossible to determine a change in a muscle relaxation state continuously on the basis of the muscle relaxation parameters which are not displayed on the monitor screen.

SUMMARY OF THE INVENTION

It is therefore an object of the invention to provide a method and a monitor apparatus which enable appropriate ascertainment of the degree of muscle relaxation, appropriate determination of timing when a muscle relaxant is to be additionally administered or an antagonist is to be administered, and accurate ascertainment of a muscle relaxation state and prediction of transition of the same.

In order to achieve the above object, according to the invention, there is provided a display method, comprising:

stimulating electrically a muscle of a patient;

detecting a response of the stimulated muscle;

obtaining a plurality of parameters indicative of muscle relaxation of the patient based on the detected response; and displaying the parameters on a display simultaneously while showing chronological changes thereof.

The parameters may include at least two of a TOF rate, a TOF count and a PTC.

According to the invention, there is also provided a monitor apparatus, comprising:

a stimulator, adapted to electrically stimulate a muscle of a patient;

a detector, adapted to detect a response of the stimulated muscle;

a processor, operable to obtain a plurality of parameters indicative of muscle relaxation of the patient based on the detected response; and a display, operable to display the parameters simultaneously while showing chronological changes thereof.

The parameters may include at least two of a TOF rate, a TOF count and a PTC.

With the above configurations, appropriate ascertainment of the degree of muscle relaxation and appropriate determination of timing when a muscle relaxant is to be additionally administered or an antagonist is to be administered are performed, so that ascertainment of a muscle relaxation state and prediction about transition of the same can be made accurately.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE EMBODIMENTS

Embodiments of the present invention will be described below in detail with reference to the accompanying drawings.

Figure 1:
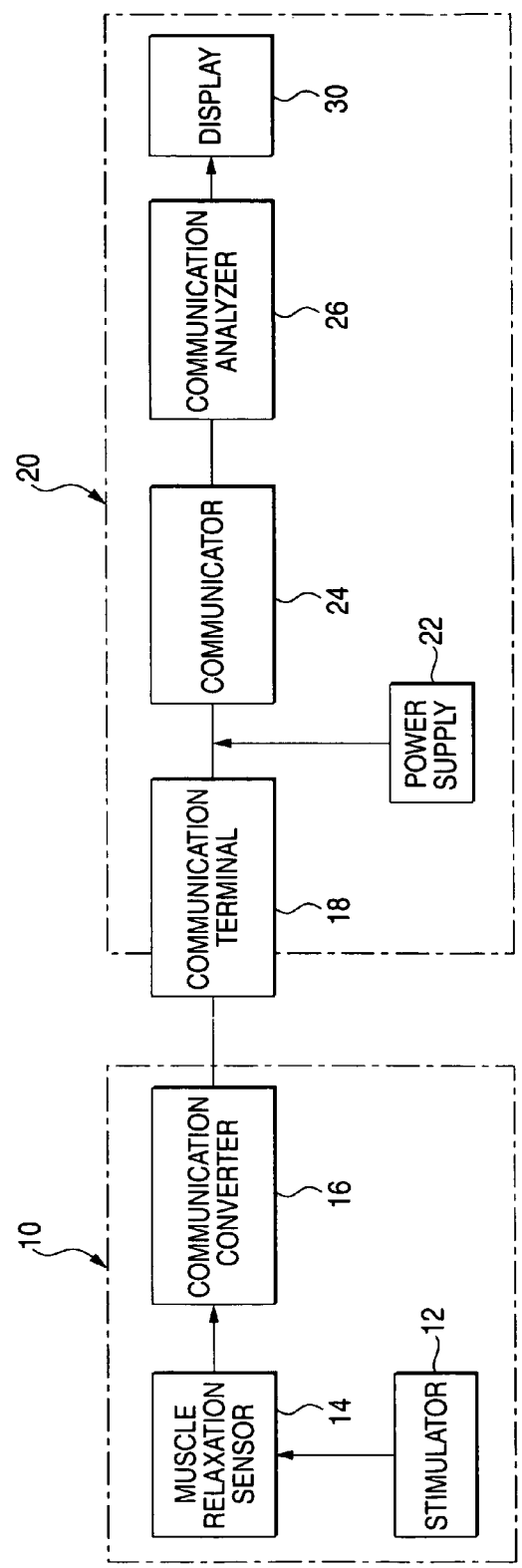
FIG. 1 is a block diagram showing a monitor apparatus according to one embodiment of the invention.
Figure 2:
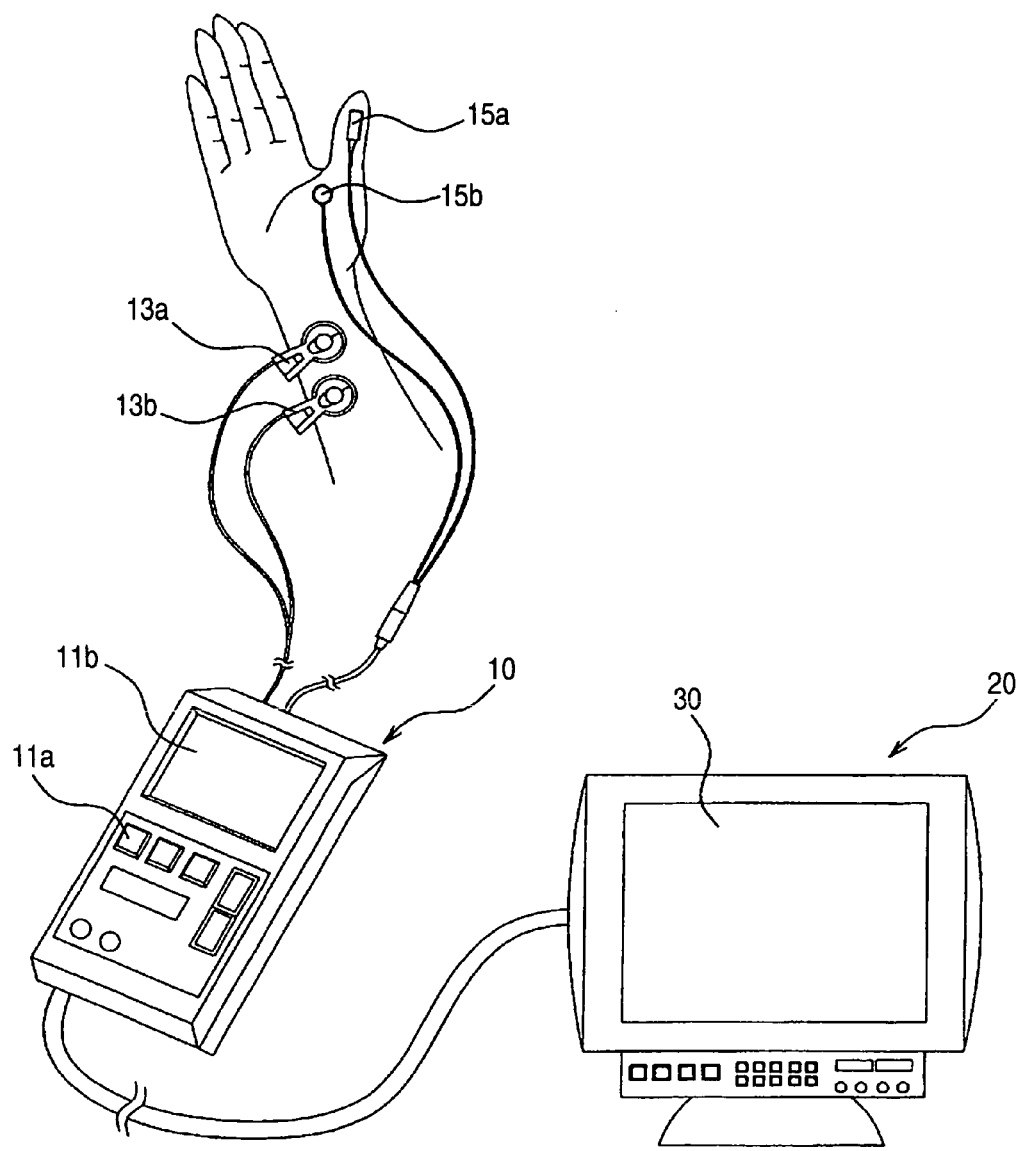
FIG. 2 is a schematic view showing the monitor apparatus.

As shown in FIGS. 1 and 2, a monitor apparatus according to one embodiment of the invention comprises a stimulation detector 10, and a bedside monitor 20 provided with a display 30.

As shown in FIG. 2, the stimulation detector 10 comprises: a button 11a for selecting an stimulation mode; a display 11b; a pair of electrode clips 13a, 13b; an acceleration sensor 15a; and a surface temperature sensor 15b. The electrode clips 13a, 13b and the sensors 15a, 15b are connected to a detector body by way of electric wires. The above members serve as a stimulator 12 and a muscle relaxation sensor 14 shown in FIG. 1.

The stimulator 12 is configured so as to be capable of applying, to predetermined positions of a patient, a plurality of types of stimulation patterns for detecting and measuring the above-described muscle relaxation state by way of the electrode clips 13a and 13b under a stimulation mode selected by the button 11a. In this case, the stimulator 12 is configured such that data pertaining to the thus-selected stimulation patterns are appropriately displayed on the display 11b.

Meanwhile, the muscle relaxation sensor 14 is configured so as to detect a muscle relaxation state of a patient by use of the acceleration sensor 15a, and measure muscle relaxation parameters, such as a TOF ratio, a TOF count, and a PTC. Meanwhile, the surface temperature sensor 15b measures a skin surface temperature of a patient under a muscle relaxation state.

As illustrated in FIG. 1, the muscle relaxation parameters detected and measured by the muscle relaxation sensor 14 are converted by a communication converter into data in a format which can be processed by the bedside monitor 20, and transferred to a communicator 24 of the bedside monitor 20 by way of a communication terminal 18. Meanwhile, reference numeral 22 denotes a power supply of the bedside monitor 20.

Thus, the data pertaining to the muscle relaxation parameters having been transferred to the communicator 24 of the bedside monitor 20 are converted again into signals which can be displayed as muscle parameters on a screen in the display 30 by a communication analyzer 26. Hence, the muscle relaxation parameters, such as the TOF ratio, the TOF count, and the PTC, are displayed on the screen in the form of numerical values or graphs.

Figure 3:
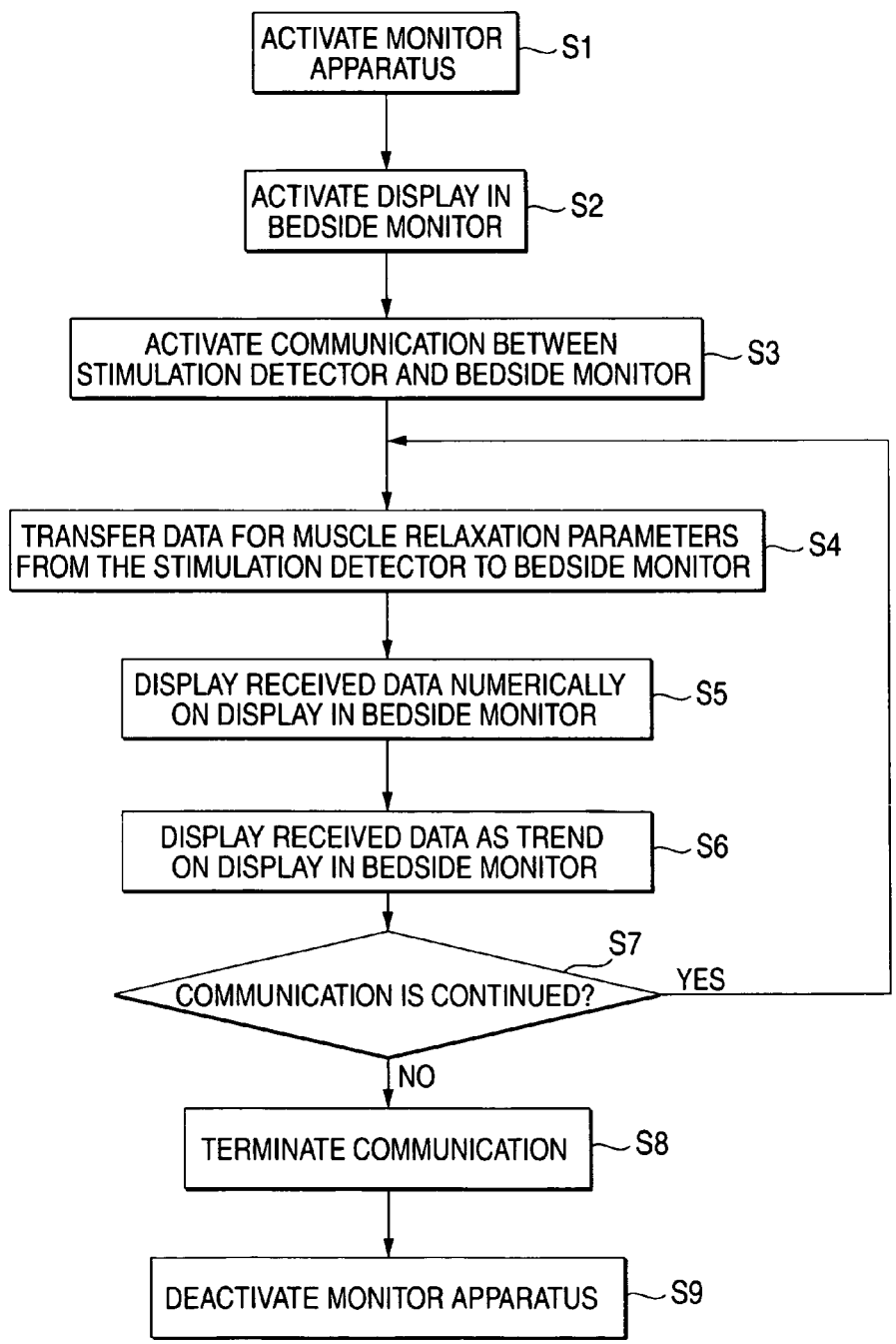
FIG. 3 is a flowchart showing operation for displaying parameters indicative of muscle relaxation which is executed in the monitor apparatus.

As shown in FIG. 3, first, the apparatus for monitoring and displaying muscle relaxation state is activated (step S1). Subsequently, the display 30 of the bedside monitor 20 is caused to display a screen (step S2). In this condition, the communicator 24 of the bedside monitor 20 starts to receive data pertaining to the muscle relaxation parameters transmitted from the stimulation detector 10 (step S3). Then, the communication analyzer 26 of the bedside monitor 20 receives data pertaining to, e.g., the TOF ratio and the TOF count (step S4). A basic screen on the display 30 displays respective numerical values (step S5). Subsequently, at least one of the TOF ratio and the TOF count is displayed on the display 30 as a trend (step S6).

Thereafter, communication status with respect to the stimulation detector 10 is ascertained in the communicator 24 of the bedside monitor 20 (step S7). When the communication is finished, receiving operation is terminated (step S8, and the monitor apparatus is deactivated (step S9). Meanwhile, there is made a setting for causing repetition of operations pertaining to step S4 through step S6 during the communication.

Figure 4:
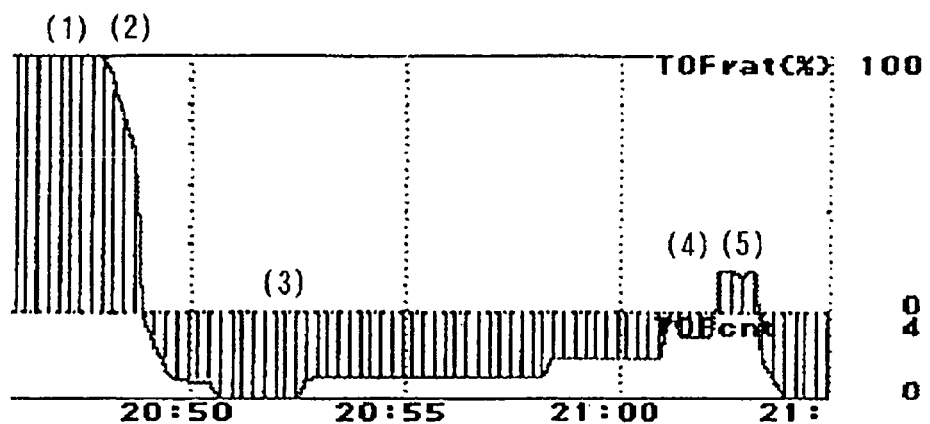
FIG. 4 shows an example of the parameters displayed on a display of a bedside monitor in the monitor apparatus.

In this embodiment, a trend of the TOF ratio and the TOF count are displayed as shown in FIG. 4. More specifically, a graph is divided along the Y-axis into an upper section and a lower section, with the X axis representing time, wherein the upper section displays a bar graph of the TOF ratio [%], and the lower section displays a bar graph of the TOF count. The drawing depicts respective state sequentially, from a measurement start point in time, wherein (1) depicts a state in which a muscle relaxant is administered, indicating the TOF ratio as 100%; (2) depicts a state of entering into a muscle relaxation state, indicating a gradual decrease in the TOF ratio; (3) depicts a deep muscle relaxation state; (4) depicts a state of starting to recover from the muscle relaxation state; and (5) depicts a state in which the muscle relaxant is administered again, whereby the patient again enters a deep muscle relaxation state.

The graph of the TOF ratio is displayed, in the upper divided section, with a first color on a background having a second color. On the other hand, the graph of the TOF count indicating the deep muscle relaxation state is displayed, in the lower divided section, with the second color on a background having the first color while sharing a temporal axis with the graph of TOF ratio. Therefore, a muscle relaxation state including the TOF ratio and the TOF count can be displayed continuously in the form of graphs. By indicating the muscle relaxation state in the form of graphs as described above, progress with time of the muscle relaxation state can be ascertained readily. Hence, there is provided an advantage of enabling accurate prediction about future transition (e.g., to be deepened or to be recovered) of the muscle relaxation state of a muscle relaxation patient.

Here, the color of the TOF count graph may not be the background color of the upper divided section so long as the background color of the lower divided section and the color of the TOF ratio graph are the same. Further, the color of the TOF ratio graph may not be the background color of the lower divided section so long as the background color of the upper divided section and the color of the TOF count graph are the same.

Figure 5:
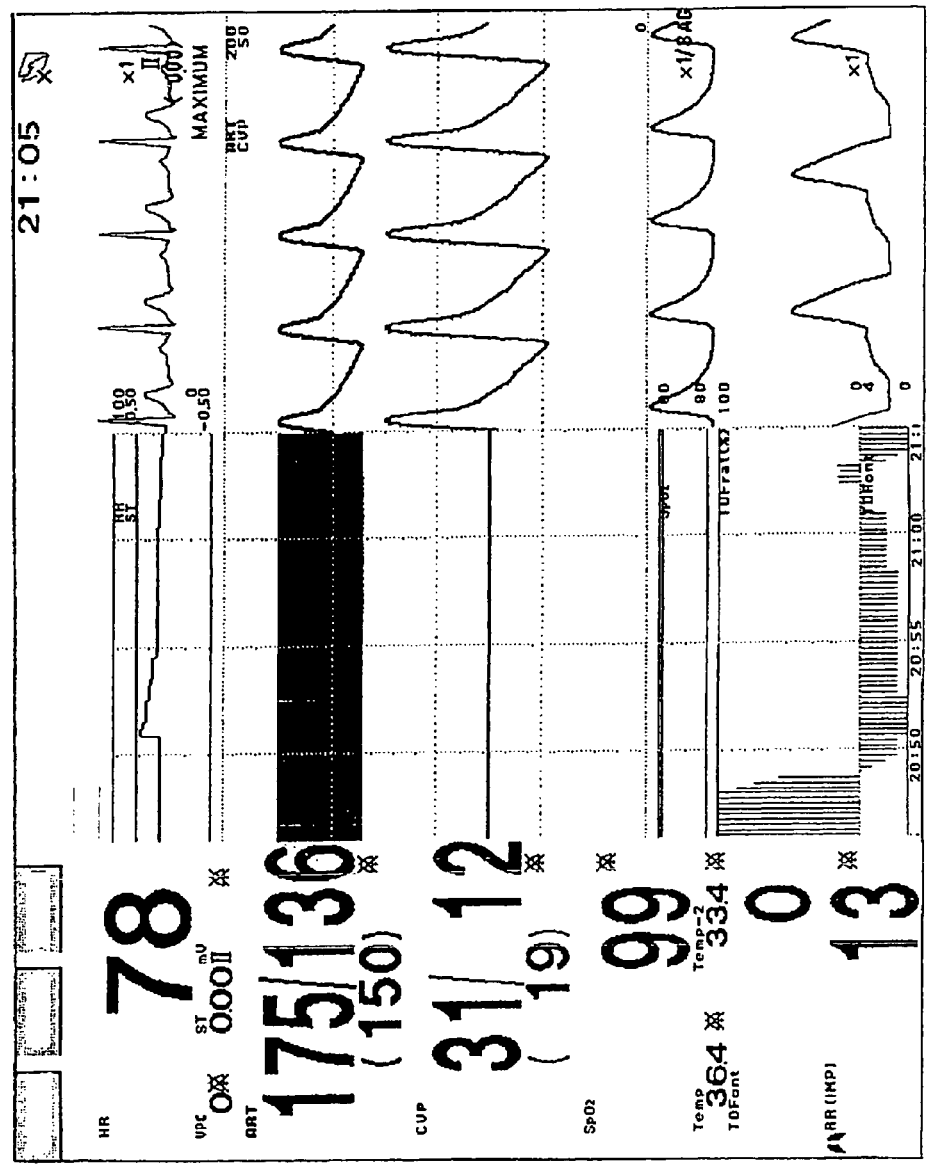
FIG. 5 shows another example of the parameters displayed on the display of the bedside monitor.

As shown in FIG. 5, the trend of the TOF ratio and the TOF count illustrated in FIG. 4 can be displayed on-screen in conjunction with vital signal parameters such as electrocardiogram, blood pressure, SpO2, body temperature, heart rate, and respiratory rate.

Although the present invention has been shown and described with reference to specific embodiments, various changes and modifications will be apparent to those skilled in the art from the teachings herein. Such changes and modifications as are obvious are deemed to come within the spirit, scope and contemplation of the invention as defined in the appended claims.

For instance, muscle relaxation parameters, such as a PTC, can be displayed in conjunction with the trend of the TOF ratio and the TOF count. In addition, a hypnotic level measured by a BIS (Bispectal Index: trademark) monitor, which is an anesthesia-related parameter, can be displayed in conjunction with the trend of the TOF ratio and the TOF count. Other than those, anesthesia-related parameters, including a number of muscle relaxation parameters, can be displayed in combination, or the like.

What is claimed is:

1. A display method, comprising:
   stimulating electrically a muscle of a patient;
   detecting a response of the stimulated muscle by an acceleration sensor;
   obtaining a plurality of parameters indicative of muscle relaxation of the stimulated muscle of the patient based on the detected response; and
   displaying the parameters on a display simultaneously while showing chronological changes thereof;
   wherein the plurality of parameters are displayed on a same graph,
   the graph is divided into an upper section and a lower section, and
   a first parameter of the plurality of parameters is displayed in the upper section of the graph extending upward from a common line and a second parameter of the plurality of parameters is displayed in the lower section of the graph downward from the common line,
   wherein the parameters include at least a TOF (train of four) rate and a TOF count.

2. The display method as set forth in claim 1, wherein a first parameter of the plurality of parameters and a second parameter of the plurality of parameters are sequentially displayed in the same graph.

3. The display method as set forth in claim 2, wherein the first and second parameters share one temporal axis in the same graph, wherein only one of the first and the second parameters is displayed at each time position on the temporal axis.

4. A monitor apparatus, comprising:
   a stimulator, adapted to electrically stimulate a muscle of a patient;
   a detector, adapted to detect a response of the stimulated muscle by an acceleration sensor;
   a processor, operable to obtain a plurality of parameters indicative of muscle relaxation of the stimulated muscle of the patient based on the detected response; and
   a display, operable to display the parameters simultaneously while showing chronological changes thereof;
   wherein the plurality of parameters are displayed on a same graph,
   the graph is divided into an upper section and a lower section, and
   a first parameter of the plurality of parameters is displayed in the upper section of the graph extending upward from a common line and a second parameter of the plurality of parameters is displayed in the lower section of the graph downward from the common line,
   wherein the parameters include at least a TOF (train of four) rate and a TOF count.

5. The monitor apparatus as set forth in claim 4, wherein a first parameter of the plurality of parameters and a second parameter of the plurality of parameters are sequentially displayed in the same graph.

6. The monitor apparatus as set forth in claim 5, wherein the first and second parameters share one temporal axis in the same graph, wherein only one of the first and the second parameters is displayed at each time position on the temporal axis.

* * * * *